(12) United States Patent
Sherman

(10) Patent No.: US 6,193,221 B1
(45) Date of Patent: Feb. 27, 2001

(54) METHOD OF AND APPARATUS FOR PRODUCING SUB-MICRON BUBBLES IN LIQUIDS, SLURRIES, AND SLUDGES

(75) Inventor: Jeffrey H. Sherman, Dallas, TX (US)

(73) Assignee: GRT, Inc., The Woodlands, TX (US)

( * ) Notice: Subject to any disclaimer, the term of this patent is extended or adjusted under 35 U.S.C. 154(b) by 0 days.

(21) Appl. No.: 09/418,101

(22) Filed: Oct. 14, 1999

Related U.S. Application Data

(63) Continuation-in-part of application No. 09/368,405, filed on Aug. 4, 1999, which is a continuation-in-part of application No. 09/224,394, filed on Dec. 31, 1998, now Pat. No. 6,129,818, which is a continuation-in-part of application No. 09/058,494, filed on Apr. 10, 1998, now Pat. No. 5,954,925.

(51) Int. Cl.[7] ........................................... B01F 3/04
(52) U.S. Cl. .......................... 261/87; 261/93; 261/122.1; 261/DIG. 70
(58) Field of Search ................................. 261/28, 32, 33, 261/83, 87, 93, 122.1, 122.2, DIG. 70; 96/291; 95/226; 55/405

(56) References Cited

U.S. PATENT DOCUMENTS

| 2,075,384 | * | 3/1937  | Vretman      | 261/93    |
| 3,118,958 | * | 1/1964  | White        | 261/122.1 |
| 4,029,724 | * | 6/1977  | Muller et al.| 261/93    |
| 4,228,112 | * | 10/1980 | Hise         | 261/93    |
| 4,521,349 | * | 6/1985  | Weber et al. | 261/93    |
| 5,954,925 | * | 9/1999  | Sherman      | 204/157.9 |

* cited by examiner

Primary Examiner—C. Scott Bushey
(74) Attorney, Agent, or Firm—Michael A. O'Neil

(57) ABSTRACT

In a method of and apparatus for producing sub-micron bubbles in liquids, slurries, and sludges, gas is maintained on the interior of the gas permeable partition at predetermined pressure. Relative movement between the gas permeable partition and the surrounding material forms sub-micron sized bubbles in the liquid, slurry, or sludge.

12 Claims, 7 Drawing Sheets

METHOD OF AND APPARATUS FOR PRODUCING SUB-MICRON BUBBLES IN LIQUIDS, SLURRIES, AND SLUDGES

CROSS REFERENCE TO RELATED APPLICATIONS

This application is a continuation-in-part of prior application Ser. No. 09/368,405, filed Aug. 4, 1999, which is a continuation-in-part of prior application Ser. No. 09/224,394 filed Dec. 31, 1998, now U.S. Pat. No. 6,129,818, which is a continuation-in-part of prior application Ser. No. 09/058,494, filed Apr. 10, 1998, now U.S. Pat. No. 5,954,925.

TECHNICAL FIELD

This invention relates generally to gas-liquid, gas-slurry, and gas-sludge reactions, and more particularly to a method of and apparatus for creating sub-micron bubbles in liquids, slurries, and sludges.

BACKGROUND OF THE INVENTION

Gas-liquid, gas-slurry, and gas-sludge reactions (hereinafter referred to collectively as gas-liquid reactions) present unique problems not found in single phase reactions. The rate and efficiency of gas-liquid reactions is dependent on the amount of contact between the gas and the liquid. The contact occurs at the interface of the liquid and the gas and is, therefore, dependent upon the surface area of the gas bubbles in the liquid. For a given amount of gas, the smaller the bubbles, the greater the surface area. It is therefore advantageous to produce smaller bubbles in order to achieve the best reaction efficiency.

The efficiency of gas-liquid reactions is particularly important in wastewater treatment systems. For example, one of the primary processes in treating municipal and some industrial wastewater streams is known as an activated sludge system. In an activated sludge system, incoming wastewater, typically under gravity flow conditions, enters a large, typically rectangular aeration basin. Within the basin a manifold system of aerators served by one or more large air compressors puts air into the wastewater. The oxygen in the air allows naturally occurring bacteria (the activated sludge) to oxidize contaminants in the wastewater.

The aerators used in conventional wastewater treatment plants are typically disks with small pores which are referred to as diffusers. Conventional diffusers are able to produce bubbles in the 100–500 micron range. These relatively large bubbles tend to rise quickly in the aeration basin, limiting the amount of oxygen that can transfer from the gas bubble to the water. As a result, extremely large quantities of air must be passed through the diffuser in order to ensure that an appropriate amount of oxygen enter the water.

Conventional diffusers tend to plug over time. When a diffuser is plugged, the air pressure behind the diffuser can blow the diffuser head completely off of the riser pipe to which it was attached. If a diffuser head blows off of the riser pipe, the pressure drop across the diffuser is eliminated. As the diffusers and riser pipes are manifolded together, any reduction in pressure drop reduces efficiency across the entire system.

Replacing a conventional diffuser requires that the activated sludge system or a portion of the system be taken off line and drained so that the diffuser may be replaced. Thus, a need exists for improvements in the art of diffuser design which facilitate the generation of sub-micron sized bubbles in the wastewater treatment systems.

Diffuser manufacturers have heretofore attempted to generate sub-micron sized bubbles in activated sludge systems by fabricating diffusers with very small outlet holes. All such attempts have been unsuccessful because the problem of diffuser plugging is exacerbated when diffuser outlet hole size is reduced.

SUMMARY OF THE INVENTION

The present invention comprises a method and apparatus which overcomes the foregoing and other difficulties that have long since characterized the prior art. In accordance with the broader aspects of the invention there is generated a stream of sub-micron sized gas bubbles. Due to their extremely small size, the gas bubbles have an extremely large surface area which increases reaction efficiency. Smaller pores in a gas permeable partition facilitate the formation of smaller bubbles. Additionally, high velocity relative movement between a liquid and the partition surface aids in shearing the bubbles off the surface while they are still small.

In accordance with first, second, and third embodiments of the invention, a gas permeable tube is positioned within an outer tube and water or other liquid is caused to continuously flow through the annular space between the two tubes. Gas is directed into the interior of the gas permeable tube and is maintained at a pressure high enough to cause gas to pass into the water or other liquid and prevent the flow of water or other liquid into the interior of the gas permeable tube. As the water or other liquid passes over the gas permeable tube, gas bubbles are continually sheared off of its surface. The gas bubbles thus generated are sub-micron in size and therefore present an extremely large surface area. The gas permeable tube may also be rotated relative to the liquid.

In accordance with a fourth embodiment of the invention, there is provided a hollow disk which supports a gas permeable partition. The disk is positioned within a water or other liquid filled container. Gas is directed into the interior of the disk and is maintained at a pressure high enough to cause gas to pass outwardly through the partition and into the water or other liquid and to prevent the flow of water or other liquid into the interior of the disk. The disk and the partition are moved at a high speed relative to the liquid. As the gas permeable partition moves relative to the water or other liquid, gas bubbles are continually sheared off of its surface. The gas bubbles thus generated are sub-micron in size and therefore present an extremely large surface area.

A fifth embodiment of the invention is particularly adapted to wastewater treatment. In accordance therewith, an activated sludge system employs a rotating diffuser, rather than the conventional static diffuser. Rotational power is supplied by air pressure flowing through jets located along the circumference of the diffuser. The rotational motion of the diffuser, coupled with the water head pressure on top of the diffuser, produces a frictional force on the small air bubbles emanating from the pores of the diffuser. This frictional force shears the air bubbles off the diffuser head before the air bubbles are completely formed, thus producing sub-micron sized bubbles and higher oxygen transfer efficiency due to the larger overall surface area. Further, the rotational motion tends to keep the pores in the diffuser cleaner than in a conventional diffuser, resulting in less plugging and thus less maintenance.

BRIEF DESCRIPTION OF THE DRAWINGS

A more complete understanding of the invention may be had by reference to the following Detailed Description when taken in conjunction with the accompanying Drawings wherein.

DETAILED DESCRIPTION

Figure 1:
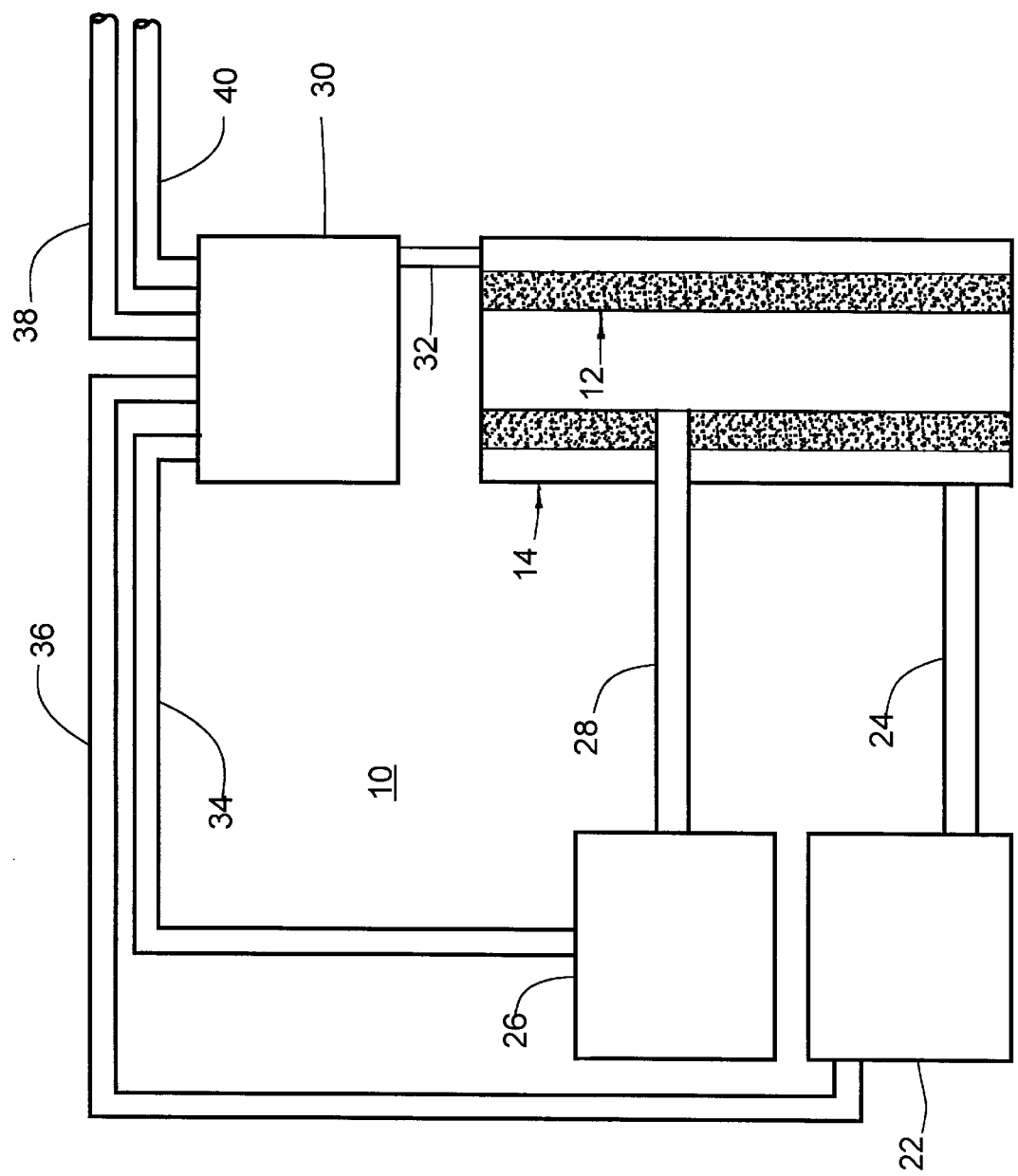
FIG. 1 is a diagrammatic illustration of a method and apparatus for producing sub-micron bubbles in liquids, slurries, and sludges comprising a first embodiment of the present invention.

Referring now to the Drawings, and particularly to FIG. 1 thereof, there is shown an apparatus for forming sub-micron bubbles in liquids, slurries, and sludges comprising a first embodiment of the invention. The apparatus 10 includes a gas permeable tube 12 positioned within an outer tube 14. The tube 12 can comprise sintered stainless steel, sintered glass, or sintered ceramic materials. As illustrated in FIG. 1, both the gas permeable tube 12 and the tube 14 comprise right circular cylinders with the tube 12 extending concentrically relative to the tube 14. Other geometrical configurations of and positional relationships between the gas permeable tube 12 and the tube 14 may be utilized in accordance with the requirements of particular applications of the invention.

In the operation of the apparatus 10, a quantity of water or other liquid is received in a reservoir 22. Water or other liquid from the reservoir 22 is directed into the annular space between the gas permeable tube 12 and the tube 14 through piping 24. During the operation of the apparatus 10, water or other liquid flows through the annulus between the gas permeable tube 12 and the tube 14 on a continuous basis.

A quantity of gas is stored in a reservoir 26. In the operation of the apparatus 10, gas is directed from the reservoir 26 into the interior of the gas permeable tube 12 through piping 28. The gas within the gas permeable tube 12 is maintained at a pressure high enough to cause the gas to pass through the walls of the tube 12 into the water or other liquid and prevent the flow of water or other liquid into the interior of the tube 12.

In the operation of the apparatus 10, the water or other liquid flowing through the annular space between the gas permeable tube 12 and the tube 14 causes gas bubbles to be continuously stripped off the exterior surface of the tube 12. In this manner the size of the gas bubbles is maintained in the sub-micron range. The sub-micron size of the gas bubbles provides an enormous surface area which in turn results in unprecedented reaction efficiency.

The water or other liquid flowing from the annulus between the gas permeable tube 12 and the tube 14 having reaction products contained therein may be directed to a distillation apparatus 30 through piping 32. If used, the distillation apparatus 30 may separate the outflow from the space between the tube 12 and the tube 14 into one or more streams 34, 36, 38, and 40.

The present invention further comprises a method of producing sub-micron bubbles in liquids, slurries, and sludges. In accordance with the method, a gas permeable tube is positioned within an outer tube. Water or other liquid is directed through the annulus between the gas permeable tube and the outer tube, and gas is directed into the interior of the gas permeable tube. The water or other liquid flowing between the gas permeable tube and the outer tube continuously strips sub-micron size bubbles from the exterior surface of the gas permeable tube.

The use of an internal gas permeable partition cylinder is shown in FIG. 1. One skilled in the art would also recognize that a vast number of shapes and orientations could be used to accomplish the same purpose. For example, the tube 14 does not need to be shaped as a tube in order to be functional as a housing. Additionally, the orientation of the gas inside an inner tube with water or other liquid between the inner tube and a housing is not required. One skilled in the art could envision a housing bisected by a gas permeable partition creating a water or other liquid chamber and a gas chamber. The only requirement of such an embodiment is that the chamber has a source of water or other liquid and a product outlet, which leads to an isolation apparatus, for example, a distillation apparatus; the gas chamber has a gas source; and the gas permeable partition allows the penetration of gas bubbles that are sheared off by the relative movement between water or other liquid in the chamber and the gas permeable membrane.

Figure 2:
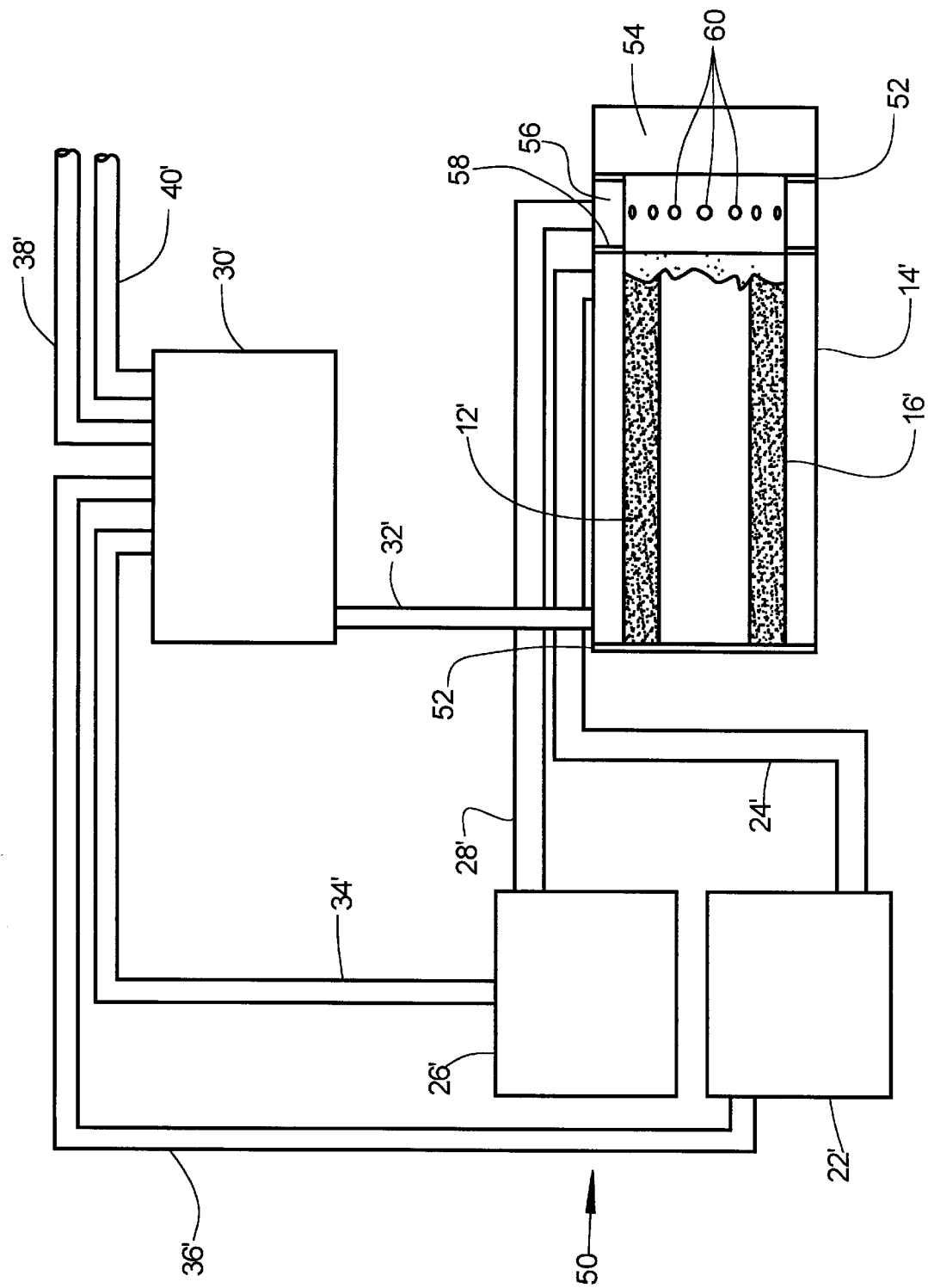
FIG. 2 is a diagrammatic illustration of a second embodiment of the apparatus of the present invention with a rotating gas permeable tube.

Referring now to FIG. 2, there is shown an apparatus for producing sub-micron bubbles in liquids, slurries, and sludges comprising a second embodiment of the invention. The apparatus 50 comprises numerous component parts which are substantially identical in construction and function to the apparatus 10 for producing sub-micron bubbles in liquids and slurries shown in FIG. 1 and described hereinabove in conjunction therewith. Such identical component parts are designated in FIG. 2 with the same reference numerals utilized in the description of the apparatus 10, but are differentiated therefrom by means of a prime (') designation.

In the apparatus 50, the gas permeable tube 12' is supported for rotation relative to the outer tube 14' by sealed bearings 52. Those skilled in the art will appreciate the fact that bearing/seal assemblies comprising separate components may be utilized in the practice of the invention, if desired.

A motor 54 is mounted at one end of the tube 14' and is operatively connected to the gas permeable tube 12' to effect rotation thereof relative to the glass tube 14'. The tube 14' includes an end portion 56 which is isolated from the remainder thereof by a seal 58. The portion of the tube 12' extending into the end portion 56 of the tube 14' is provided with a plurality of uniform or nonuniform apertures 60.

In the operation of the apparatus 50, gas is directed from the reservoir 26' through the piping 28' through the end portion 56 of the tube 14' and through the apertures 60 into the interior of the gas permeable tube 12'. Water or other liquid flows from the reservoir 22' through the piping 24' into the portion of the tube 14' that is isolated from the end portion 56 by the seal 58. Water or other liquid flows out of the tube 14' through piping 32' to a distillation apparatus 30', or other receiving apparatus.

The operation of the apparatus for producing sub-micron bubbles 50 of FIG. 2 differs from the operation of the apparatus 10 of FIG. 1 in that in the operation of the apparatus 50, the relative movement between the bubbles forming on the surface of the gas permeable tube 12' and the water or other liquid contained within the tube 14' is controlled by the motor 54 rather than the flow rate of the water or other liquid as it passes through the tube 14'. This is advantageous in that it allows the gas permeable tube 12' to be rotated at a relatively high velocity relative to the water or other liquid contained within the tube 14', thereby assuring that sub-micron size bubbles will be sheared from the surface of the gas permeable tube 12'. Meanwhile, the velocity of the water or other liquid passing through the interior of the glass tube 12' can be relatively slow, thereby assuring a maximum number of sub-micron size bubbles entering the water or other liquid per unit volume thereof.

As will be understood by those skilled in the art, relative movement between the exterior surface of the gas permeable tube 12' and the water flowing through the tube 14' depends both on the speed of rotation of the tube 12' under the action of the motor 54 and the rate of flow of the water through the tube 14'. Thus, the tube 12' must rotate faster when the water flow rate is relatively low and need not rotate as fast when the water flow rate is relatively high. Feedback components for controlling the rotational speed of the tube 12' as a function of the water flow rate may be utilized in the practice of the invention, if desired.

Figure 3:
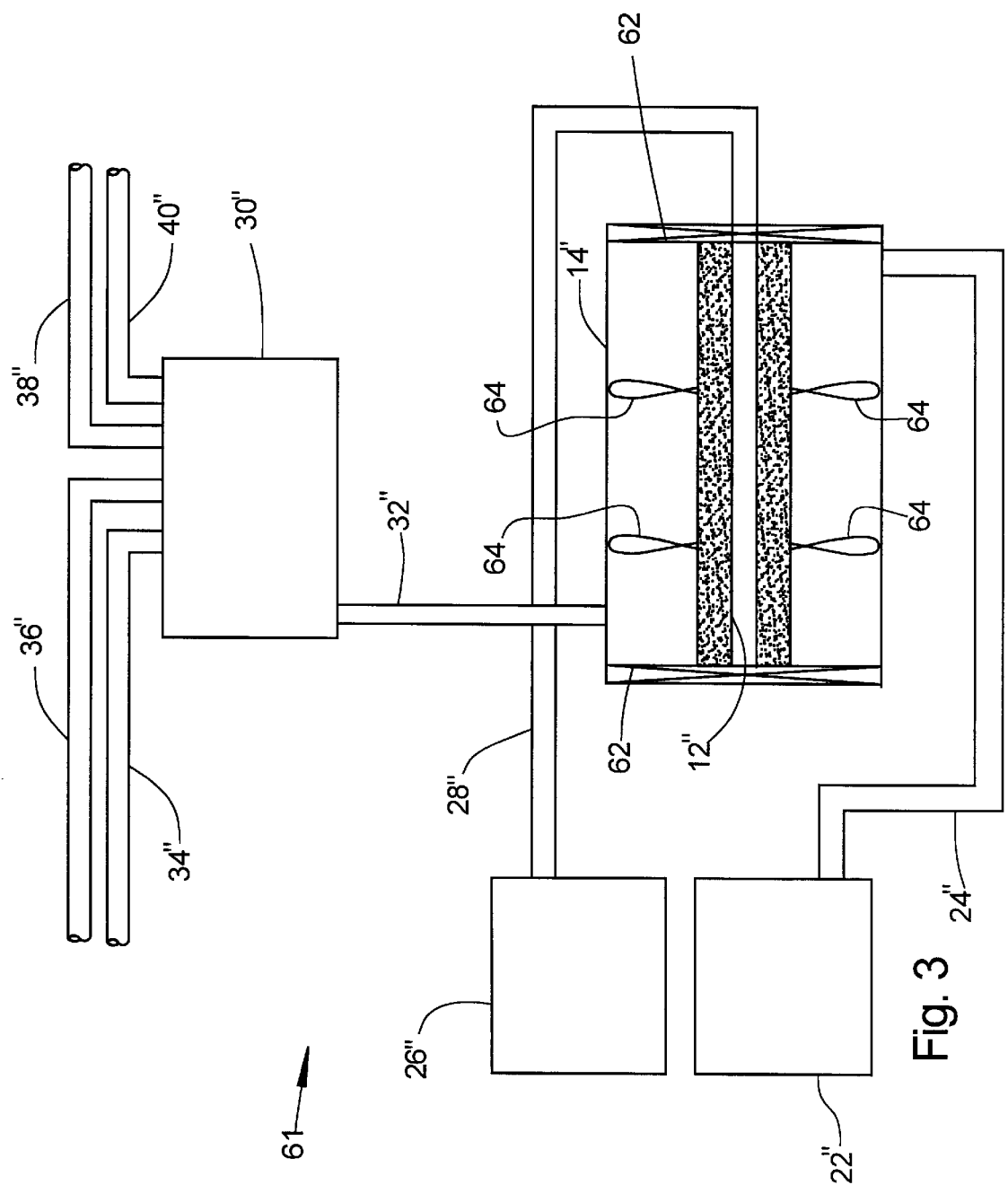
FIG. 3 is a diagrammatic illustration of a third embodiment of the apparatus of the present invention with a rotating gas permeable tube with turbines.

An apparatus 61 for producing sub-micron bubbles comprising a third embodiment of the invention is illustrated in FIG. 3. The apparatus 61 comprises numerous component parts which are substantially identical in construction and function to component parts of the apparatus 10 illustrated in FIG. 1 and described hereinabove in conjunction therewith. Such identical component parts are designated in FIG. 3 with the same reference numerals utilized in the description of the apparatus 10, but are differentiated therefrom by means of a double prime (") designation.

The apparatus 61 comprises a gas permeable tube 12" which is supported for rotation relative to the outer tube 14" by sealed bearings 62. Those skilled in the art will appreciate the fact that the apparatus 61 may be provided with bearing/seal assemblies comprising separate components, if desired.

The gas permeable tube 12" is provided with one or more turbines 64. The pitch of the turbines 64 is adjusted to cause the tube 12" to rotate at a predetermined speed in response to a predetermined flow rate of water or other liquid through the tube 14".

Similarly to the apparatus of FIG. 2, the use of the apparatus 61 is advantageous in that the gas permeable tube 12" can be caused to rotate relatively rapidly in response to a relatively low flow rate of water or other liquid through the glass tube 14". This assures that sub-micron size bubbles will be stripped from the outer surface of the gas permeable tube 12" and that a maximum number of bubbles will be received in the water or other liquid flowing through the glass tube 14" per unit volume thereof. The use of the apparatus 61 is particularly advantageous in applications of the invention wherein water or other liquid flows through the system under the action of gravity, in that the use of the turbines 64 eliminates the need for a separate power source to effect rotation of the gas permeable tube 12" relative to the glass tube 14".

Figure 4:
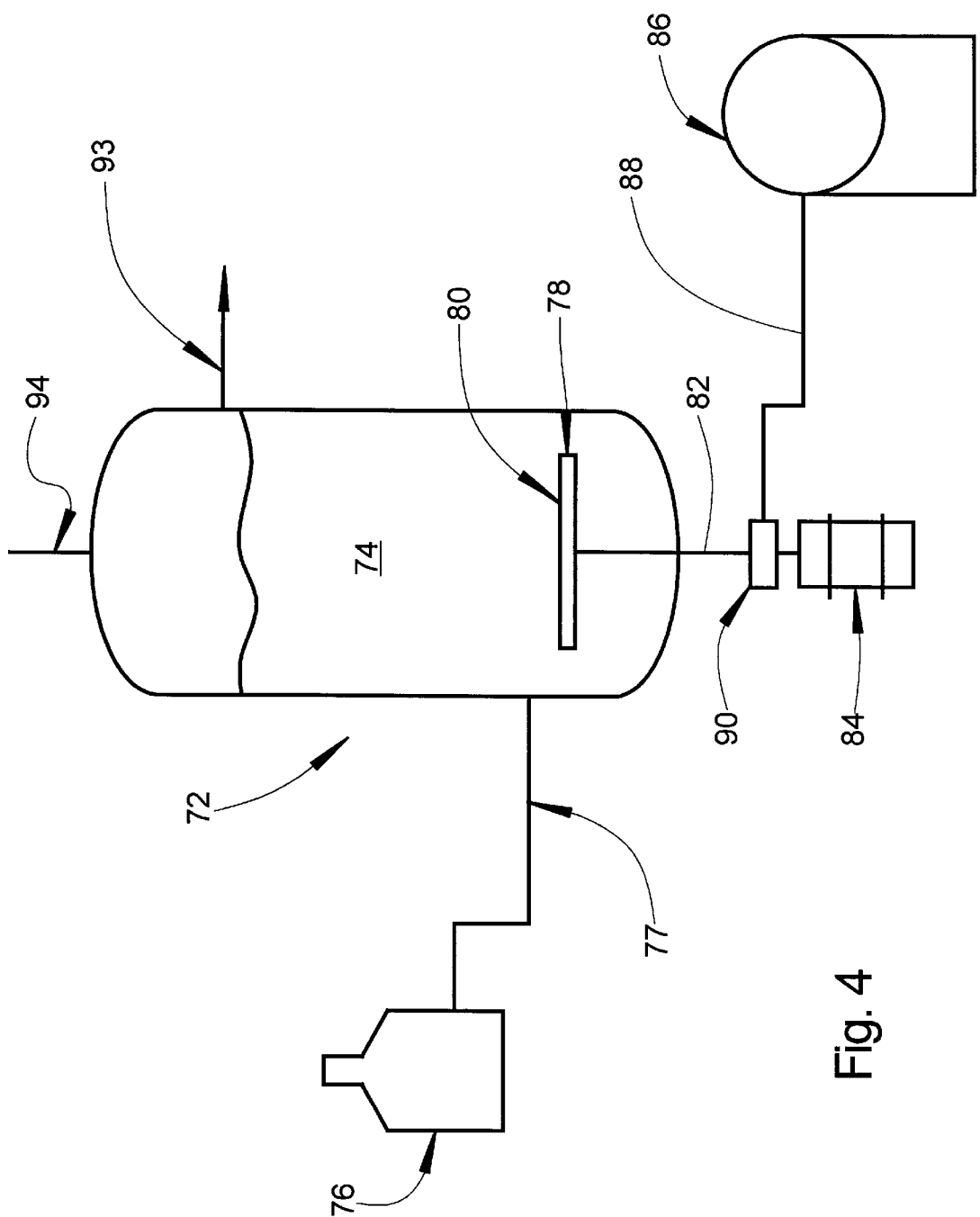
FIG. 4 is a diagrammatic illustration of a fourth embodiment of the apparatus of the present invention.
Figure 5:
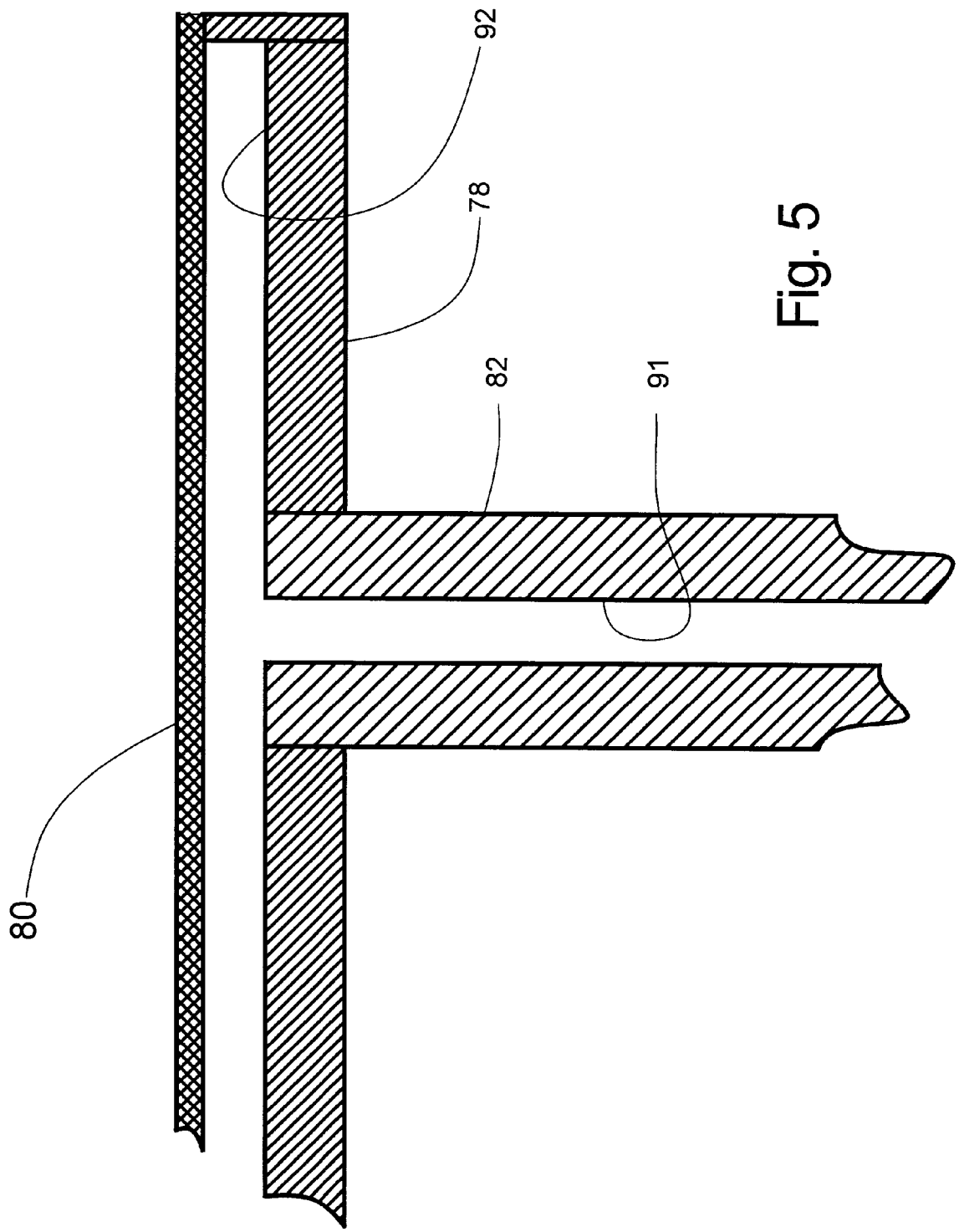
FIG. 5 is an enlargement of a portion of FIG. 4.

Referring now to FIGS. 4 and 5, there is shown a method of and apparatus for producing sub-micron bubbles in liquids, slurries, and sludges 70 comprising a fourth embodiment of the invention. In accordance with a fourth embodiment of the invention, there is provided a tank 72 having a quantity of water or other liquid 74 contained therein. Water or other liquid is supplied to the tank 72 from a source 76 through piping 77.

A hollow disk 78 is mounted in the lower portion of the tank 72. As is best shown in FIG. 5, the disk 78 includes a gas permeable partition 80 supported on a tube 82 for rotation within the tank 72 under the operation under the motor 84. The partition 80 may comprise sintered stainless steel, sintered glass, or sintered ceramic materials depending upon the requirements of particular applications of the invention. Gas received from a supply 86 is directed through piping 88 and a suitable commutator 90 into the tube 82 and through the tube 82 into the interior of the hollow disk 78. The tube 82 has a hollow interior 91 and the disk 78 has a hollow interior 92 connected in fluid communication therewith.

The disk 78 is supplied with gas at a pressure just high enough to overcome the head pressure of the water or other liquid 74. The disk 78 is rotated by the motor 84 at an appropriate speed in contact with the water or other liquid 74 such that a shearing phenomenon occurs at the surface of the gas permeable partition 80 thus producing bubbles of extremely small, i.e., sub-micron, size. The extreme small size of the bubbles thus produced results in a surface area to volume ratio of small bubbles which significantly improves the efficiency of the reaction. Liquid is recovered from the tank 72 through outlet 93 and gas is recovered from the tank 72 through outlet 94.

Figure 6:
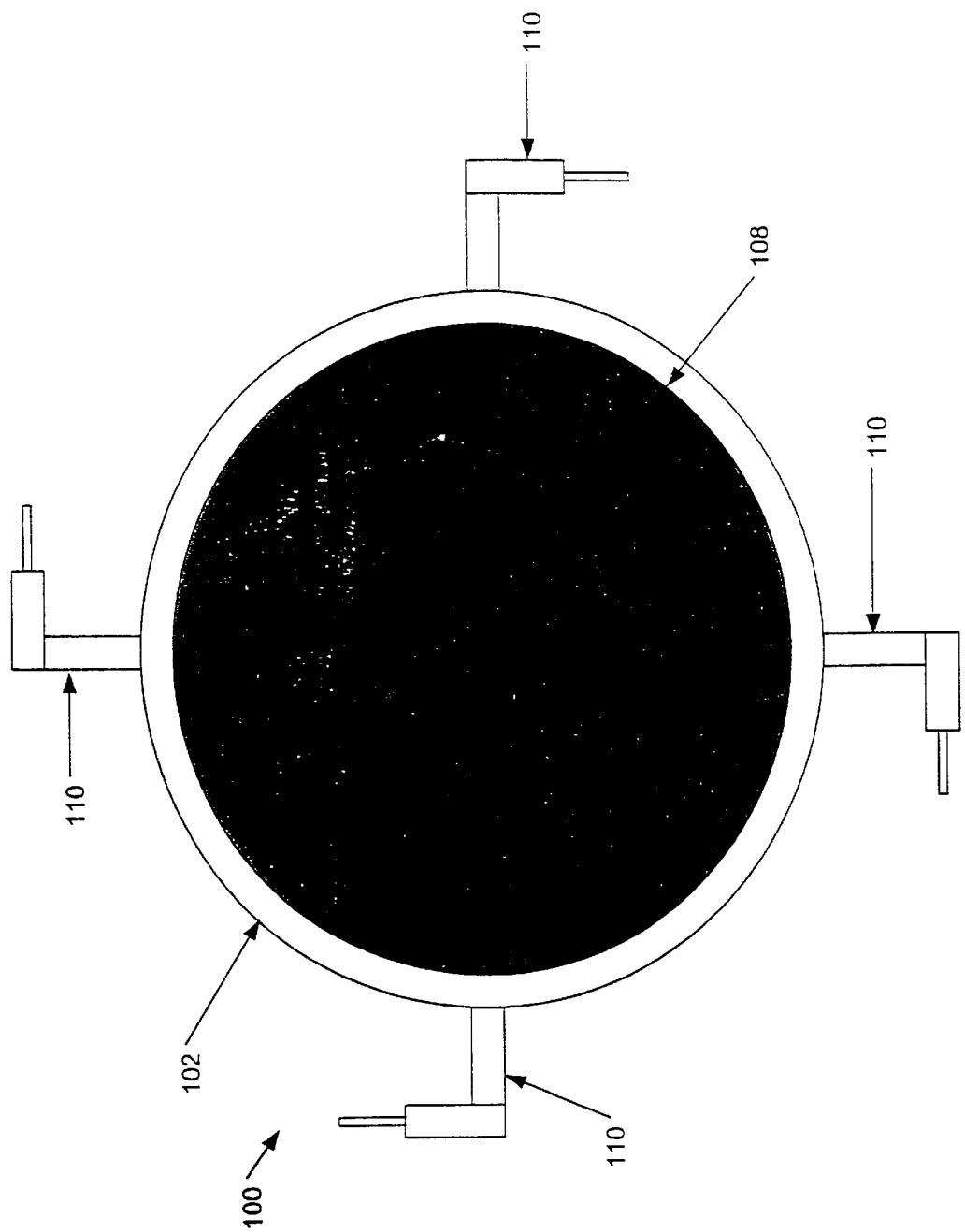
FIG. 6 is a diagrammatic illustration of a fifth embodiment of the invention.
Figure 7:
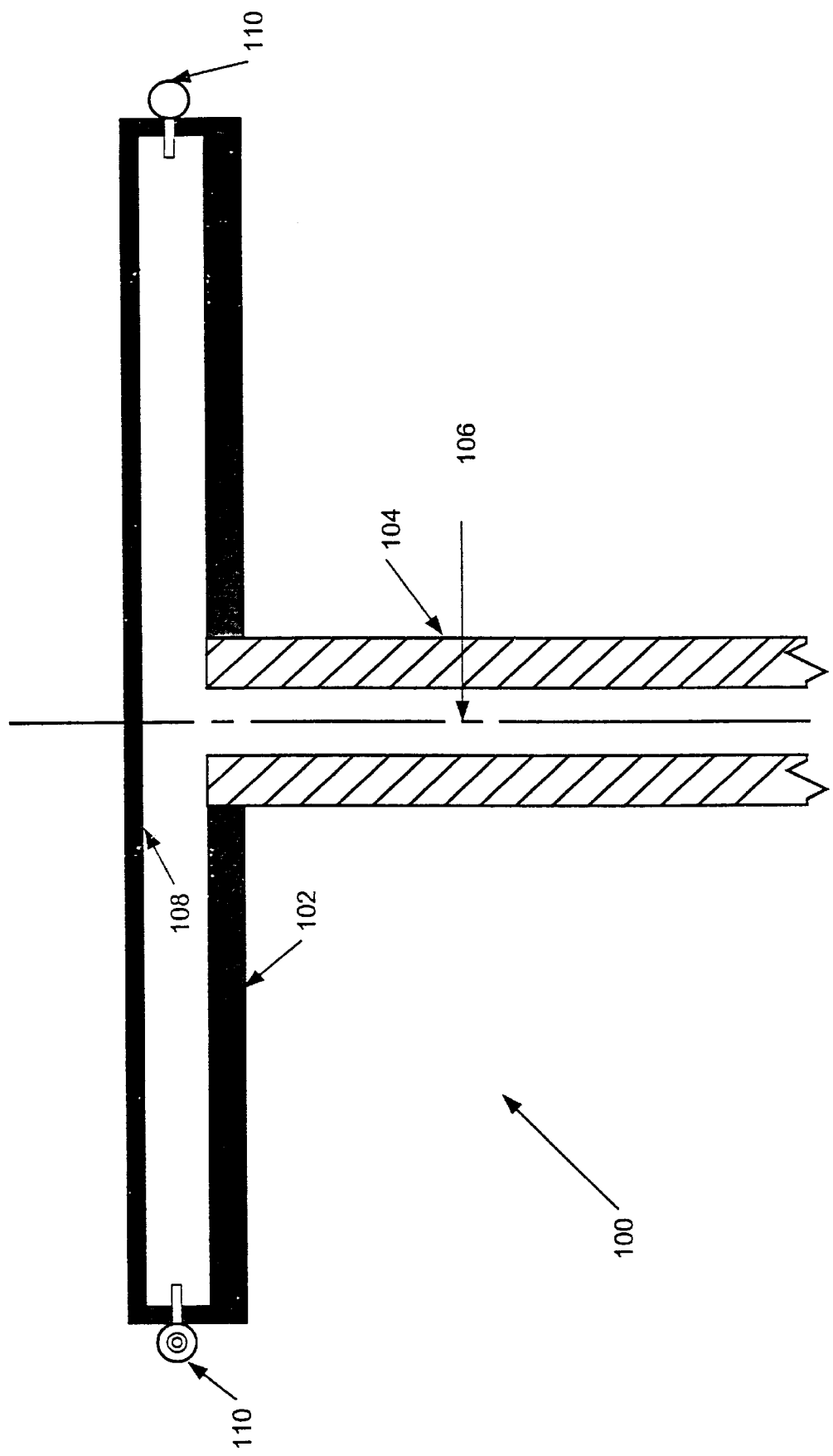
FIG. 7 is a further illustration of the embodiment of FIG. 6.

Referring to FIGS. 6 and 7, there is shown a diffuser for activated sludge systems 100 comprising a fifth embodiment of the invention. The diffuser 100 includes a hollow disk 102 which is supported on a tube 104 for rotation about a nominally vertical axis 106. The hollow disk 102 is provided with a gas permeable partition 108 which may be formed from sintered stainless steel or other materials depending upon the requirements of particular applications of the invention. A plurality of propulsion jets 110 are located at spaced intervals around the periphery of the hollow disk 102.

In the operation of the fifth embodiment of the invention, a plurality of hollow disks 102 are situated in a quantity of sludge comprising suspended solid matter produced by wastewater treatment processes, sewage treatment processes, industrial wastewater treatment processes, etc. Compressed air is continually directed through the tube 104 into the hollow disk 102. Compressed air continually flows outwardly from the hollow disk 102 both through the gas permeable partition 108 and the propulsion jets 110. Discharge of compressed air from the propulsion jets 110 causes rotation of the hollow disk 102 and the tube 104 about the axis 106, it being understood that the hollow disk 102 may be supported for rotation independently of the tube 104, if desired.

The discharge of compressed air through the gas permeable partition 108 produces sub-micron sized bubbles in the liquids surrounding the hollow disk 102. The rotation of the gas permeable partition 108 under the action of the propulsion jets 110, coupled with the water head pressure on top of the gas permeable partition 108, produces a frictional force on the sub-micron sized bubbles emanating from the gas permeable partition which shears the bubbles from the gas permeable partition before they are completely formed. In this manner there is produced sub-micron sized air bubbles and higher oxygen transfer efficiency due to the larger overall surface area. Additionally, the rotation of the gas permeable partition 108 tends to keep the pores thereof cleaner than is the case in the conventional diffuser, resulting in a substantial reduction in plugging and in turn a substantial reduction in maintenance.

Although preferred embodiments of the invention have been illustrated in the accompanying Drawing and described in the foregoing Detailed Description, it will be understood that the invention is not limited to the embodiments disclosed but is capable of numerous rearrangements, modifications, and substitutions of parts and elements without departing from the spirit of the invention.

I claim:

1. An apparatus for producing sub-micron bubbles in a quantity of sludge comprising:

a hollow chamber positioned in the sludge and including a gas permeable partition engaging the sludge;

apparatus for maintaining gas within the interior of the hollow chamber at a predetermined pressure sufficient to cause gas flow through the gas permeable partition while preventing the flow of liquid from the sludge therethrough; and at least one propulsion jet mounted on the hollow chamber and connected in fluid communication therewith for discharging a gas jet and thereby causing relative movement between the gas permeable partition and the sludge.

2. The apparatus according to claim 1 wherein the gas permeable partition comprises a sintered stainless steel partition.

3. The apparatus according to claim 1 wherein the gas permeable partition comprises a sintered glass partition.

4. The apparatus according to claim 1 wherein the gas permeable partition comprises a sintered ceramic partition.

5. The apparatus according to claim 1 wherein the hollow chamber comprises a hollow disk.

6. The apparatus according to claim 1 wherein the propulsion jet causes rotation of the gas permeable partition relative to the sludge.

7. A method for producing sub-micron bubbles in liquids comprising:

providing a quantity of sludge;

providing a hollow chamber including a gas permeable partition;

positioning the partition of the hollow chamber in the sludge;

maintaining gas within the interior of the hollow chamber at a predetermined pressure sufficient to cause gas flow through the gas permeable partition while preventing the flow of liquid from the sludge therethrough; and discharging a gas jet from the hollow chamber and thereby causing relative movement between the gas permeable partition and the sludge.

8. The method according to claim 7 wherein the gas permeable partition comprises a sintered stainless steel partition.

9. The method according to claim 7 wherein the gas permeable partition comprises a sintered glass partition.

10. The method according to claim 7 wherein the gas permeable partition comprises a sintered ceramic partition.

11. The method according to claim 7 wherein the hollow chamber comprises a hollow disk and wherein the gas jet is discharged relatively tangentially thereto.

12. The method according to claim 7 wherein the step of causing relative movement between the gas permeable partition and the sludge comprises rotating the gas permeable partition relative to the sludge under the action of the gas jet.

* * * * *